United States Patent [19]

Keil

[11] Patent Number: 5,075,492

[45] Date of Patent: Dec. 24, 1991

[54] METHOD OF MANUFACTURING CYCLOOCTANEDICARBOXYLIC ACID DIESTERS

[75] Inventor: Thomas Keil, Marl, Fed. Rep. of Germany

[73] Assignee: Huels Aktiengesellschaft, Marl, Fed. Rep. of Germany

[21] Appl. No.: 524,913

[22] Filed: May 18, 1990

[30] Foreign Application Priority Data

May 27, 1989 [DE] Fed. Rep. of Germany ....... 3917329

[51] Int. Cl.$^5$ ............................................. C07C 67/36
[52] U.S. Cl. .................................................. 560/114
[58] Field of Search ................................ 560/114, 233

[56] References Cited

U.S. PATENT DOCUMENTS

| | | | |
|---|---|---|---|
| 2,448,368 | 8/1946 | Gresham | 560/114 |
| 2,805,245 | 9/1957 | Natta | 560/114 |
| 3,462,481 | 8/1969 | Rudkovsky | 562/497 |
| 3,481,975 | 12/1969 | Rudkovsky | 562/497 |
| 3,507,891 | 4/1970 | Hearne | 560/233 |
| 3,856,832 | 12/1974 | Ethyl Corporation | 560/114 |
| 3,906,016 | 9/1975 | Isa | 560/114 |
| 3,935,228 | 1/1976 | Keblys | 560/233 |
| 3,946,055 | 3/1976 | Isa | 560/233 |
| 3,952,034 | 4/1976 | Thompson | 562/497 |
| 3,976,670 | 8/1976 | Fanning | 560/233 |
| 3,980,683 | 9/1976 | Isa | 560/233 |
| 4,041,057 | 8/1977 | Fanning | 560/114 |
| 4,404,394 | 9/1983 | Isoyai | 560/204 |
| 4,539,424 | 9/1985 | Jenck | 560/114 |

FOREIGN PATENT DOCUMENTS 3308882 9/1984 Fed. Rep. of Germany ...... 560/114

OTHER PUBLICATIONS

Matsuda, Bull. Chem. Soc. Jap., 46, pp. 524–530 (1973).

*Primary Examiner*—Michael L. Shippen
*Attorney, Agent, or Firm*—Oblon, Spivak, McClelland, Maier & Neustadt

[57] ABSTRACT

A method of manufacturing cyclooctanedicarboxylic acid diesters by hydrocarboxyalkylation of 1,5-cyclooctadiene over a cobalt catalyst in the presence of tertiary amines is disclosed.

7 Claims, No Drawings

METHOD OF MANUFACTURING CYCLOOCTANEDICARBOXYLIC ACID DIESTERS

BACKGROUND OF THE INVENTION

1. Field of the Invention

The invention relates to methods for manufacturing cyclooctanedicarboxylic acid diesters by hydrocarboxyalkylation of 1,5-cyclooctadiene.

2. Discussion of the Background

Cyclooctanedicarboxylic acid diesters are valuable intermediate products in the manufacture of alkyd resins, polyamides, polyesters, and lubricants.

According to Falbe, J., 1967, "Synthesen mit Kohylenmonoxid", pp. 102 ff., cyclooctanedicarboxylic acid diesters can be produced by hydrocarboxyalkylation of 1,5-cyclooctadiene over palladium catalysts. The same reaction should lead only to saturated cyclooctanecarboxylic acid esters if carried out over solid cobalt catalysts.

According to Belgian Patent No. 613,730, in the hydrocarboxylation of 1,5-cyclooctadiene with carbon monoxide and water over nickel catalysts (which method is analogous to hydrocarboxyalkylation), only the saturated cyclooctanecarboxylic acid is produced.

Heretofore, cyclooctanedicarboxylic acid diesters could be produced from 1,5-cyclooctadiene only with the aid of palladium catalysts. There is a need however for a method for producing cyclooctanedicarboxylic acid diesters from 1,5-cyclooctadiene using a non-noble metal compound-containing catalyst composition.

SUMMARY OF THE INVENTION

Accordingly, it is an object of this invention to provide a method for producing cyclooctanedicarboxylic acid diesters from 1,5-cyclooctadiene using a non-noble metal compound-containing catalyst composition.

The inventor has now surprisingly discovered that this object, and other objects of this invention which will become apparent from the description of the invention given hereinbelow, are satisfied by carrying out the hydrocarboxyalkylation in the presence of a cobalt compound and a tertiary amine at a temperature of 100° to 200° C. and a pressure of 150 to 350 bar.

DETAILED DESCRIPTION OF THE PREFERRED EMBODIMENTS

Suitable cobalt compounds which can be used include hydrogen cobalt tetracarbonyl, $HCo(CO)_4$. One may also use however (1) cobalt salts, such as cobalt-(II) acetate, cobalt-(II) naphthenate, cobalt-(II) stearate, cobalt-(II) carbonate, or cobalt-(II) chloride; (2) cobalt oxides; or (3) cobalt complexes, such as dicobalt octacarbonyl.

In the initial phase of the hydrocarboxyalkylation these cobalt compounds require, in addition to carbon monoxide, 0.1 to 10 mol% hydrogen (based on the moles of carbon monoxide). Under these reaction conditions of a temperature of 100° to 200° C. and a pressure of 150 to 350 bar hydrogen cobalt tetracarbonyl forms. This is putatively the actual catalytically active compound. The formation of the hydrogen cobalt tetracarbonyl is generally completed in about one-half hour.

When hydrogen cobalt tetracarbonyl is employed, a certain small initial content of hydrogen is helpful, because hydrogen regenerates spent catalyst.

The amount of cobalt compound used is preferably 0.5 to 5 mol% (based on the amount of 1,5-cyclooctadiene used).

Candidates for use as the tertiary amine which serves as a promoter are pyridine and non-ortho-, mono-or poly-$C_{1-3}$-alkylated pyridines, e.g. 3- and 4-picoline, 3,4- and 3,5-lutidine, and 3- and 4-ethylpyridine. Preferably, 4-picoline is used. The molar ratio of tertiary amine to cobalt compound is preferably 2:1 to 10:1.

The solvent/reagents used are generally $C_{1-6}$ linear, branched or cyclic alcohols, such as methanol, ethanol, iso-propanol, butanol, or hexanol. Methanol is preferred. Preferably a molar ratio of 1,5-cyclooctadiene to alcohol of 1:2 to 1:4 is used. The alcohol used provides the alcoholic moiety of the ester product.

Within the stated temperature range, preferably the temperature is initially lower and subsequently elevated. Thus, in the first stage, the temperature is preferably 120° to 150° C. and in the second stage it is 150° to 200° C. A pressure of preferably 200 to 300 bar is preferred during the hydrocarboxyalkylation. The reaction is generally carried out in an autoclave.

The total reaction time is usually 24 to 48 hrs. The cyclooctanedicarboxylic acid di-$C_{1-6}$-esters can be isolated from the reaction mixture by customary methods. Isomeric mixtures are always obtained.

The present method requires no noble metal catalysts. Relatively more economical catalysts may be used instead.

The yields of cyclooctanedicarboxylic acid di-$C_{1-6}$-esters obtained are usually above 50 wt.%. The interfering saturated cyclooctanecarboxylic acid esters are produced in amounts of only 10 to 20%. Another major by-product are the corresponding cyclooctanecarboxylic acid esters. These can be resubjected to hydrocarboxyalkylation after the main product is separated out. The result is increased yield of the desired product.

Having generally described this invention, a further understanding can be obtained by reference to certain specific examples which are provided herein for purposes of illustration only and are not intended to be limiting.

EXAMPLES

Experimental protocol used

A 5-liter "VA" steel autoclave was used.

The reaction components, vis. 1,5-cyclooctadiene, the alcohol, the cobalt-(II) salt, and 4-picoline, were charged and brought to reaction temperature. Then pressurized hydrogen was added, followed by pressurized carbon monoxide, whereby the total pressure was established. The decrease in pressure during the reaction was compensated by continuous addition of carbon monoxide. After completion of the reaction, the mixture was cooled to room temperature and depressurized. The yields, determined by gc, are given in mol% on the basis of the 1,5-cyclooctadiene employed.

EXAMPLE 1

Composition of the reaction mixture 951.5 g (8.8 mol) 1,5-cyclooctadiene,
592.1 g (18.5 mol) methanol,
98.3 g (1.06 mol) 4-picoline,
155.6 g (0.26 mol) Co-(II) naphthenate (Co content 1?%).

Reaction conditions $P_{H2}$ = 10 bar (initial).
$P_{total}$ = 280 bar.
1st stage: 140° C., 24 hr.
2nd stage: 190° C., 12 hr.

Results 4.5% of bicyclo[3.3.1]non-2-ene-9-one.
10% of cyclooctanecarboxylic acid methyl ester,
17% of cyclooctanecarboxylic acid methyl ester, and
47% of cyclooctanedicarboxylic acid dimethyl ester.
78.5% = Total.

The residue contained isomerized starting product, and high-boiling materials. In a fractional distillation, the diester (isomeric mixture) distilled over at a temperature of 110° to 120° C. and 0.9 mbar. The product was identified by gc and ms.

EXAMPLE 2

Composition of the reaction mixture 951.5 g 1,5-cyclooctadiene,
592.1 g methanol,
98.3 g 4-picoline,
155.6 g Co-(II) naphthenate (Co content 10%).

Reaction conditions $P_{H2}$ = 10 bar (initial).
$P_{total}$ = 180 bar.
1st stage: 140° C., 24 hr.
2nd stage: 170° C., 12 hr.

Results 5.3% of bicyclo[3.3.1]non-2-ene-9-one,
13% of cyclooctanecarboxylic acid methyl ester,
13.4% of cyclooctanecarboxylic acid methyl ester,
54% of cyclocctanedicarboxylic acid dimethyl ester.
85.7% = Total.

EXAMPLE 3

Composition of the reaction mixture 951.5 g 1,5-cyclooctadiene,
592.1 g methanol,
98.3 g 4-picoline,
155.6 g Co-(II) naphthenate (Co content 10%).

Reaction conditions $P_{H2}$ = 10 bar (initial).
$P_{total}$ = 280 bar.
1st stage: 140° C., 24 hr.
2nd stage: 160° C., 12 hr.

Results 5.3% of bicyclo[3.3.1]non-2-ene-9-one,
13.5% of cyclooctanecarboxylic acid methyl ester,
12.3% of cyclooctanecarboxylic acid methyl ester,
54% of cyclooctanedicarboxylic acid dimethyl ester.
85.1% = Total.

EXAMPLE 4

Composition of the reaction mixture 1005.5 g 1,5-cyclooctadiene,
625.7 g methanol,
103.9 g 4-picoline,
69.5 g Co-(II) acetate.4 H$_2$O.

Reaction conditions $P_{H2}$ = 10 bar (initial).
$P_{total}$ = 270 bar.
1st stage: 140° C., 24 hr.
2nd stage: 160° C., 12 hr.

Results 6.2% of bicyclo[3.3.1]non-2-ene-9-one,
12.1% of cyclooctenecarbcxylic acid methyl ester,
12.4% of cyclooctanecarboxylic acid methyl ester,
54.8% of cyclooctanedicarboxylic acid dimethyl ester.
85.5% = Total.

EXAMPLE 5

Composition of the reaction mixture 832.5 g 1,5-cyclooctadiene,
744.9 g ethanol,
86.0 g 4-picoline,
136.1 g Co-(II) naphthenate (Co content 10%).

Reaction conditions $P_{H2}$ = 10 bar (initial).
$P_{total}$ = 280 bar.
1st stage: 140° C., 24 hr.
2nd stage: 160° C., 12 hr.

Results 5.9% of bicyclo[3.3.1]non-2-ene-9-one,
11.7% of cyclooctanecarboxylic acid ethyl ester,
15.2% of cyclooctanecarboxylic acid ethyl ester,
57.3% of cyclooctanedicarboxylic acid diethyl ester.
90.1% = Total.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for manufacturing a cyclooctanedicarboxylic acid di-$C_{1-6}$-ester, consisting essentially of reacting 1,5-cyclooctadiene with carbon monoxide and a $C_{1-6}$ alcohol in the presence of a cobalt compound and a tertiary amine at a temperature of 100° to 200° C. and a pressure of 200 to 300 bar, the molar ratio of said tertiary amine to said cobalt compound being 2:1 to 10:1.

2. The method of claim 1, wherein a cobalt salt, a cobalt oxide, a cobalt complex, or a mixture thereof, is used as said cobalt compound.

3. The method of claim 1, wherein pyridine or a non-ortho-substituted $C_{1-3}$-alkylpyridine, or both, is used as said tertiary amine.

4. The method of claim 1, wherein 4-picoline is used as said tertiary amine.

5. The method of claim 1, wherein the reaction is carried out in methanol.

6. The method of claim 1, wherein the reaction is carried out in two stages: a first stage at a temperature of 120° to 150° C., and a second stage at a temperature of 150° of 200° C.

7. The method of claim 1, wherein said cobalt compound is used in an amount of 0.5 to 5 mol% based on the amount of said 1,5-cyclooctadiene used.

* * * * *